(12) United States Patent
Abdullah et al.

(10) Patent No.: US 11,008,541 B2
(45) Date of Patent: May 18, 2021

(54) STACKED MEMBRANE BIOREACTOR

(71) Applicant: Battelle Memorial Institute, Columbus, OH (US)

(72) Inventors: Zia Abdullah, Bexley, OH (US); Michael L. Dickens, Westerville, OH (US); Micah Paul McCreery, Baltimore, OH (US); Randy L. Jones, Delaware, OH (US); Elvin Ray Beach, III, Columbus, OH (US); Jon-David S. Sears, Columbus, OH (US); Erin Suzanne Schultz, Dublin, OH (US); Stephanie Ann Smith, Columbus, OH (US); Paul E. George, II, Powell, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 436 days.

(21) Appl. No.: 15/484,084

(22) Filed: Apr. 10, 2017

(65) Prior Publication Data

US 2017/0321180 A1    Nov. 9, 2017

Related U.S. Application Data

(62) Division of application No. 14/367,231, filed as application No. PCT/US2012/070686 on Dec. 19, 2012, now abandoned.

(Continued)

(51) Int. Cl.
*C12M 3/00* (2006.01)
*C12M 1/00* (2006.01)

(Continued)

(52) U.S. Cl.
CPC ............ *C12M 29/04* (2013.01); *C12M 23/24* (2013.01); *C12M 23/34* (2013.01); *C12M 23/40* (2013.01);

(Continued)

(58) Field of Classification Search
CPC ....... C12M 25/02; C12M 23/40; C12M 23/24
See application file for complete search history.

(56) References Cited

U.S. PATENT DOCUMENTS 3,711,259 A    1/1973  Gurney
4,661,458 A *  4/1987  Berry ..................... C12M 23/34
                                                              210/321.75

(Continued)

FOREIGN PATENT DOCUMENTS

CN    101451103 A    6/2009
EP    0363262 A1     4/1990

(Continued)

OTHER PUBLICATIONS

International Search Report and Written Opinion in International Application No. PCT/US2012/070686, dated Jul. 15, 2013 (10 pages).

*Primary Examiner* — Nathan A Bowers
(74) *Attorney, Agent, or Firm* — Benesch, Friedlander, Coplan & Aronoff LLP

(57) ABSTRACT

Scalable biomaterial-based bioreactors are described. In one embodiment, the bioreactor may comprise perforated plates stacked such that the assembled bioreactor has the necessary manifolds and chambers to transport gas and liquids to a biomaterial contained within the bioreactor, and to remove the reaction products. In another embodiment, single use bioreactors are described. Methods of operating the bioreactors are also described.

16 Claims, 6 Drawing Sheets

Related U.S. Application Data

(60) Provisional application No. 61/577,225, filed on Dec. 19, 2011.

(51) Int. Cl.
  *C12M 1/04* (2006.01)
  *C12M 1/34* (2006.01)
  *C12P 3/00* (2006.01)

(52) U.S. Cl.
  CPC ............ *C12M 23/44* (2013.01); *C12M 41/00* (2013.01); *C12P 3/00* (2013.01)

(56) References Cited

U.S. PATENT DOCUMENTS

| | | | | |
|---|---|---|---|---|
| 4,937,196 A | * | 6/1990 | Wrasidlo | C12M 23/04 435/297.2 |
| 4,940,547 A | * | 7/1990 | Cho | C02F 3/102 210/643 |
| 4,976,931 A | | 12/1990 | Stoermer, III | |
| 5,686,304 A | * | 11/1997 | Codner | C12M 23/14 435/283.1 |
| 6,228,607 B1 | | 5/2001 | Kersten et al. | |
| 6,844,187 B1 | * | 1/2005 | Wechsler | C12M 29/04 435/297.2 |
| 7,560,274 B1 | * | 7/2009 | Fuller | C12M 23/24 383/102 |
| 2004/0045890 A1 | | 3/2004 | Herczeg | |
| 2006/0014274 A1 | | 1/2006 | Klaus | |
| 2007/0042490 A1 | * | 2/2007 | Welter | C12M 23/24 435/325 |
| 2011/0143334 A1 | | 6/2011 | Roscoe | |
| 2011/0226686 A1 | | 9/2011 | Maurer | |
| 2014/0323694 A1 | * | 10/2014 | Von Keitz | C12M 29/04 530/350 |

FOREIGN PATENT DOCUMENTS

| | | |
|---|---|---|
| WO | 96/26264 A | 8/1996 |
| WO | 2011139804 A2 | 11/2011 |

* cited by examiner

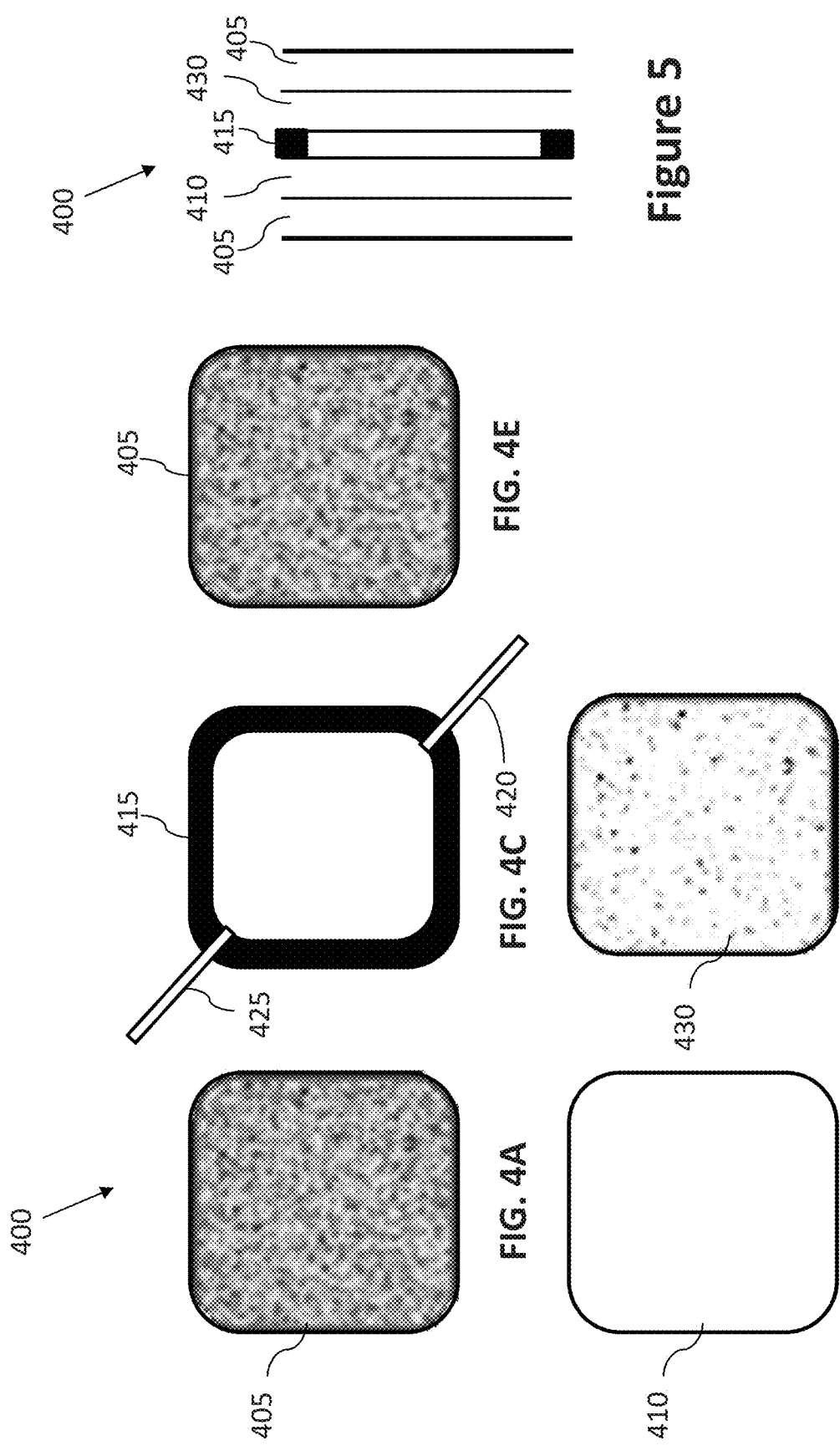

STACKED MEMBRANE BIOREACTOR

CROSS-REFERENCE TO RELATED APPLICATIONS

This application is a divisional of U.S. patent application Ser. No. 14/367,231, filed on Jun. 19, 2014, which is a National stage entry under 35 U.S.C. § 371 of PCT Pat. App. No. PCT/US2012/070686, filed Dec. 19, 2012, which claims priority from U.S. Provisional Pat. App. Ser. No. 61/577,225, filed Dec. 19, 2011, the entirety of each of which are incorporated by reference herein.

STATEMENT REGARDING FEDERALLY SPONSORED RESEARCH OR DEVELOPMENT

This invention was made with government support under DE-AR0000095 awarded by The Advanced Research Projects Agency-Energy (ARPA-E) to The Ohio State University. The government has certain rights in the invention.

BACKGROUND $CO_2$ is produced in many commercial processes. Excessive emission of $CO_2$ is damaging to the atmosphere. Thus, it would be desirable to capture and use at least some of the $CO_2$ produced in commercial processes, if only to reduce $CO_2$ emissions into the atmosphere.

One potential use for the $CO_2$ produced in commercial processes is in the production of short and medium-length alkanols for, e.g., fuel. For example, ethanol and butanol may be used as fuel in an internal combustion engine. Butanol's longer hydrocarbon chain causes it to be fairly non-polar and, thus, butanol is more similar to gasoline than ethanol is. In fact, butanol has been demonstrated to work in vehicles designed for use with gasoline without modification.

Toward this end, bioreactors are being investigated to produce products, including fuels, from $CO_2$, $H_2$, and $O_2$. Two basic methods appear promising: One involves biomaterials that use sunlight to convert $CO_2$, such as phototrophic bacteria or algae; and another involves biomaterials that can use $H_2$ directly and do not require sunlight, such as some types of bacteria.

However, there are a number of practical problems in developing bioreactors. One problem relates to the biological aspect of the bioreactors, e.g., what biomaterial to use (bacteria or algae, and what type), and how and whether to modify the biomaterial. Another problem involves the design of the bioreactor. For example, supply of $H_2$ and $O_2$ to the biomaterial involves significant safety issues because of the potentially explosive nature of the mixture of the gases.

What is needed is a safe, scalable bioreactor that efficiently converts $CO_2$, $H_2$, and $O_2$, and perhaps other hydrocarbons or other carbon/hydrogen-rich compounds (in gas or liquid form) into useful products, including, but not limited to, fuels.

SUMMARY

In one embodiment, a bioreactor is provided, the bioreactor comprising: a biomaterial reactor chamber; a gas reactor chamber in fluid communication with a first side of the biomaterial reactor chamber; a medium reactor chamber in fluid communication with a second side of the biomaterial reactor chamber; a gas inlet and a gas outlet in fluid communication with the gas reactor chamber; and a medium inlet and a medium outlet in fluid communication with the medium reactor chamber.

In another embodiment, a bioreactor is provided, the bioreactor comprising: a manifold plate having a gas inlet, a gas outlet, a medium inlet, and a medium outlet; a gas delivery plate having a gas reactor chamber, a gas inlet manifold in fluid communication with the gas reactor chamber and the gas inlet, a gas outlet manifold in fluid communication with the gas reactor chamber and the gas outlet, a medium inlet manifold in fluid communication with the medium inlet, and a medium outlet manifold in fluid communication with the medium outlet; a biomaterial plate having a biomaterial reactor chamber, a gas inlet manifold in fluid communication with the gas delivery plate gas inlet manifold, a gas outlet manifold in fluid communication with the gas delivery plate gas outlet manifold, a medium inlet manifold in fluid communication with the gas delivery plate medium inlet manifold, and a medium outlet manifold in fluid communication with the gas delivery plate medium outlet manifold; a medium delivery plate having a medium reactor chamber, a gas inlet manifold in fluid communication with the biomaterial plate gas inlet manifold, a gas outlet manifold in fluid communication with the biomaterial plate gas outlet manifold, a medium inlet manifold in fluid communication with the medium reactor chamber and the biomaterial plate medium inlet manifold, and a medium outlet manifold in fluid communication with the medium reactor chamber and the biomaterial plate medium outlet manifold; and an end plate.

In another embodiment, a bioreactor is provided, the bioreactor comprising: a first outer shell; a hydrophilic membrane; a biomaterial; a hydrophobic membrane; optionally, a flame arrestor; and a second outer shell.

In another embodiment, a method for making a bio-based product is provided, the method comprising: introducing $H_2$ gas into a bioreactor on a first side of a biomaterial reactor chamber containing biomaterial; introducing medium containing $O_2$ into the bioreactor on a second side of the biomaterial reactor chamber; introducing $CO_2$ into the bioreactor on the first side, the second side, or both, wherein the biomaterial produces the bio-based product from the $H_2$, the $CO_2$, and the $O_2$; and outletting and/or removing the bio-based product from the bioreactor.

BRIEF DESCRIPTION OF THE DRAWINGS

The accompanying figures, which are incorporated in and constitute a part of the specification, illustrate various example systems, methods, results, and so on, and are used merely to illustrate various example embodiments. It should be noted that various components depicted in the figures may not be drawn to scale, and that the various shapes (e.g., rectangular, square) depicted in the figures are presented for purposes of illustration only, and should not be considered in any way as limiting.

FIG. 4A is an illustration of an end layer 405 of a membrane assembly 400 for a stacked bioreactor.

FIG. 4B is an illustration of a gas permeable membrane 410 of a membrane assembly 400 for a stacked bioreactor.

FIG. 4C is an illustration of a spacer layer 415 of a membrane assembly 400 for a stacked bioreactor.

FIG. 4D is an illustration of a liquid permeable membrane 430 of a membrane assembly 400 for a stacked bioreactor.

FIG. 4E is an illustration of an end layer 405 of a membrane assembly 400 for a stacked bioreactor.

FIG. 5 is an illustration of one embodiment of membrane assembly 400 for use in a stacked bioreactor.

DETAILED DESCRIPTION

Figure 1:
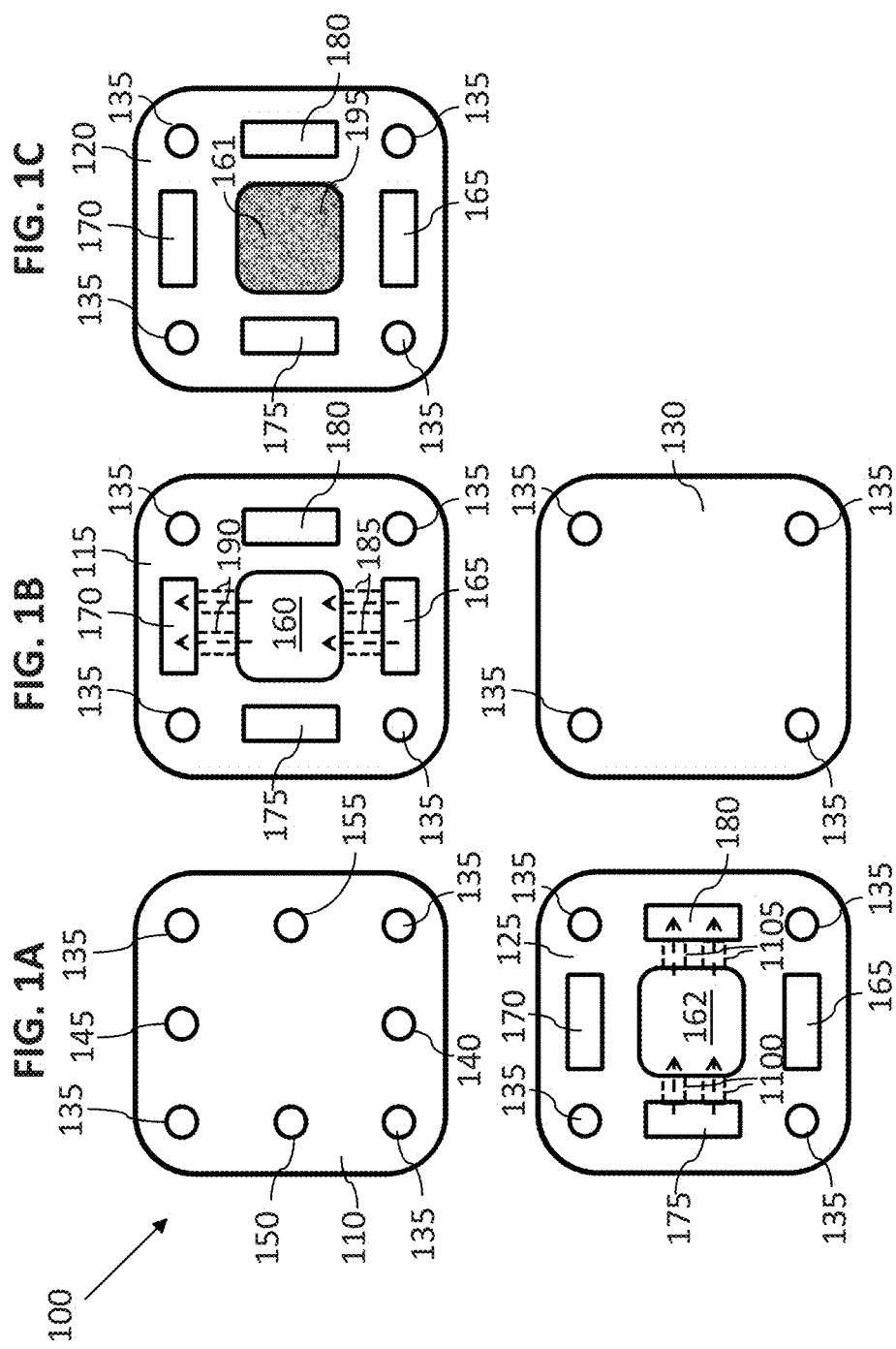
FIG. 1A is an illustration of a manifold plate 110 used in one embodiment of a stacked bioreactor 100.
FIG. 1B is an illustration of a gas delivery plate 115 used in one embodiment of a stacked bioreactor 100.
FIG. 1C is an illustration of a biomaterial plate 120 used in one embodiment of a stacked bioreactor 100.
FIG. 1D is an illustration of a medium delivery plate 125 used in one embodiment of a stacked bioreactor 100.
FIG. 1E is an illustration of an end plate 130 used in one embodiment of a stacked bioreactor 100.

The invention involves novel, safe, scalable, biomaterial-based bioreactors and method of using the same. In one embodiment, the bioreactor is made using perforated plates stacked such that the assembled bioreactor has the necessary manifolds and chambers to transport gas and liquids to the biomaterial and to remove the reaction products.

In one embodiment, the bioreactor may be used to contact gases and liquid medium with a reactor chamber containing biomaterial. As used herein, the term "biomaterial" is intended, at a minimum, to cover all types of biomaterial that can be used to convert $CO_2$ to bio-based products, including but not limited to, bacteria and algae. The term "biomaterial" may also include biomaterial that does not use and/or require $CO_2$. In one embodiment, the biomaterial comprises a living organism capable of using hydrogen gas as a source of energy. In one embodiment, the biomaterial comprises bacteria capable of using hydrogen gas as a source of energy. In one embodiment, the biomaterial is an autotroph. In one embodiment, the biomaterial comprises *Ralstonia eutropha*, e.g., H16 or *Cupriavidus*. In another embodiment, the reactor may be used to grow anaerobic organisms (using oxygen nonpermeable membranes about the biomaterial) and aerobic organisms that use alternative carbon sources.

In one embodiment, the biomaterial reactor chamber may contain a natural or artificial biofilm grown on a membrane or other fibrous support structure, or the biomaterial can be sandwiched in a chamber cavity between two membranes. On one side of the biomaterial reactor chamber containing the biomaterial, a gas, such as hydrogen, may be introduced. On the opposite side of the chamber, a liquid medium, providing nutrients, oxygen, and carbon dioxide for the biomaterial may be circulated. Thus, in at least one embodiment, when a first element is said to be "in fluid communication with" a second element (e.g., a gas reactor chamber "in fluid communication with" a first side of the biomaterial reactor chamber; or a medium reactor chamber "in fluid communication with a second side of the biomaterial reactor chamber") in fact, the two elements may be in fluid communication through the membrane(s).

The liquid medium may comprise any suitable liquid medium that may supply nutrients and oxygen, and, in some embodiments, carbon dioxide, such as are well known in the art. For example, the liquid medium may comprise Repaske's medium or a modified version thereof. The biomaterial converts the carbon dioxide to bio-based products or another product(s), which can be outletted or otherwise removed on either the gas side or the liquid medium side.

In various embodiments, the bioreactor may be used to make bio-based products, including, but not limited to, lubricants and greases, lubricant additives, biofuels, bio-based chemicals, oil remediation dispersants and sorbents, health supplements, nutraceutical, cosmeceutical, and pharmaceutical product ingredients, horticultural and aquacultural feed or supplements, and intermediates to the foregoing. As used herein, the term "biofuels" broadly refers to bio-based products suitable for use as a fuel or a combustion source, including fuels suitable for transportation and power generation. Biofuels include, but are not limited to, biogasoline, biodiesel, jet fuels, ethanol, methanol, butanol, and the like. Bio-based materials and chemicals include, but are not limited to: Polyhydroxyalkanoates, lactic acid, acetic acid, succinic acid, malic acid, 1-butanol, isobutanol, 2-butanol, other alcohols, amino acids, 1,3-propanediol, ethylene, glycerine, β-lactam antibiotics, cephalosporin, alkanes, terpenes, and the like.

In one embodiment, the bioreactor may be made up of a stack of plates. Each plate may be stamped with a perforation pattern such that when the plates are stacked together, a bioreactor is created, with gas and medium reactor chambers on each side of a biomaterial reactor chamber containing the biomaterial. Gas may be supplied on one side of the biomaterial reactor chamber through gas manifolds, and medium may be supplied on the other side of the biomaterial reactor chamber through medium manifolds.

In some embodiments, costs for preparation of the bioreactor may be minimized because the plates can be mass produced using a stamping process. In addition, in some embodiments, reactor capacity may be readily scalable by increasing the number of plates in the stack and/or the dimensions of the membranes. The reactor may also provide increased safety, as the small size of each individual cell will limit the magnitude of potentially destructive energy release. If desirable or appropriate, flame arrestors may be added in the gas manifolds, as well as between the plates, to prevent flame propagation if hydrogen and oxygen were to react explosively.

In some embodiments, the reactor may be configured so that different reactions take place in adjacent cells. In one embodiment, the stacked reactors may be configured so that products produced in one reactor become feedstocks for another reactor, and so forth, like a daisy chain to the final product. For example:

Stack Reactor 1=Product 1 (feedstock for Reactor 2)→Stack Reactor 2=Product 2 (feedstock for Reactor 3)→→→final product.

For example, hydrogen can be produced by one type of biomaterial in one cell, and this hydrogen can be transported to an adjacent cell, where it can be used as a feedstock to produce a secondary product. In another example, other intermediates (e.g., metabolites, peptides, building blocks) may be prepared and/or supplied for more complex products. Indeed, using such a design may provide for practically limitless bioconversions (e.g., chiral specific conversions of pharmaceuticals and their precursors, as well as oxygenation and/or dehydrogenation and/or methylation and/or acetylation, of numerous compounds). The possibilities are vast and, in view of disclosure of the present application, achievable.

In one embodiment, $CO_2$ may be supplied in the form of $CO_2$ emitted from a commercial process. In one embodiment, $CO_2$, $H_2$, and hydrocarbon or hydrocarbon-like (hydrogen and carbon-rich) gas may be supplied in the form of a product from pyrolysis of a biomass.

Figure 2:
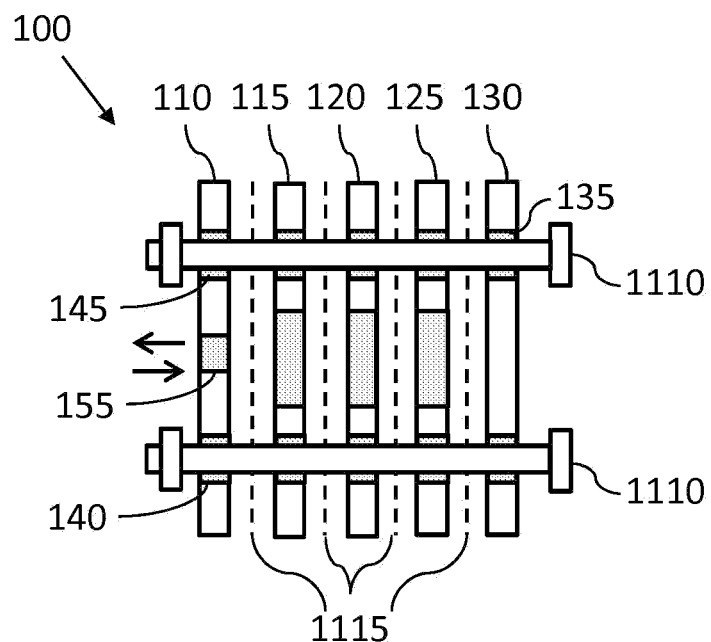
FIG. 2 is an illustration of one embodiment of an assembled stacked bioreactor 100.

FIGS. 1-2 illustrate one embodiment of a bioreactor 100. More specifically, FIGS. 1A-E illustrate a series of plates that can be used to form one embodiment of bioreactor 100. FIG. 1A illustrates manifold plate 110. FIG. 1B shows a gas delivery plate 115. FIG. 1C shows a biomaterial plate 120. FIG. 1D shows a medium delivery plate 125. And FIG. 1E shows an end plate 130.

The plates can be made of any suitable material, such as metal, plastic, ceramic, acrylic, polycarbonate, polypropylene, Delrin® manufactured by Dupont, polyetheretherketone, polyvinyl chloride (PVC), stainless steel, and the like. The plates can be any suitable shape, such as square, rectangular, circular, and the like.

The bioreactor may be secured together in any suitable manner, as would be understood by those of skill in the art. For example, bolts, screws, or clamps may be used. In some embodiments, adjacent plates could have interlocking parts to secure the adjacent plates together. The interlocking parts may be releasable or permanent. For instance, permanent interlocks may be used if the bioreactor was to be disposable and not intended to be disassembled. In one embodiment, each of the plates has bolt holes 135 on the corners for bolting the plates together to assemble the bioreactor.

As shown, manifold plate 110 has a gas inlet 140 and a gas outlet 145 on two opposing sides, and a medium inlet 150 and medium outlet 155 on the other two opposing sides of manifold plate 110.

As shown, gas delivery plate 115 has a gas reactor chamber 160 in the middle, biomaterial plate 120 has a biomaterial reactor chamber 161 in the middle, and medium delivery plate 125 has a medium reactor chamber 162 in the middle. Gas delivery plate 115 has a gas inlet manifold 165 and a gas outlet manifold 170 on opposite sides of the plate outside of gas reactor chamber 160, and a medium inlet manifold 175 and a medium outlet manifold 180 outside of gas reactor chamber 160 on the other two opposing sides. Biomaterial plate 120 has a gas inlet manifold 165 and a gas outlet manifold 170 on opposite sides of the plate outside of biomaterial reactor chamber 161, and a medium inlet manifold 175 and a medium outlet manifold 180 outside of biomaterial reactor chamber 161 on the other two opposing sides. Medium delivery plate 125 has a gas inlet manifold 165 and a gas outlet manifold 170 on opposite sides of the plate outside of medium reactor chamber 162, and a medium inlet manifold 175 and a medium outlet manifold 180 outside of medium reactor chamber 162 on the other two opposing sides.

As shown, gas delivery plate 115 has gas inlet channels 185 between gas inlet manifold 165 and gas reactor chamber 160, and gas outlet channels 190 between gas reactor chamber 160 and gas outlet manifold 170.

Biomaterial plate 120 may have a membrane 195 in biomaterial reactor chamber 161. In one embodiment, membrane 195 may contain an artificial or natural biofilm which is used to immobilize biomaterial. Membrane 195 may be fabricated using composite materials and may serve to provide one or more of the following attributes: (a) structural support or scaffolding to the biofilm; (b) a seal between the gas and the medium phases; and (c) pathways for the gases, nutrients, and products to and from the biomaterial immobilized in the biofilm. Alternatively, biomaterial reactor chamber 161 may contain free-floating biomaterial.

As shown, medium delivery plate 125 has medium inlet channels 1100 between medium inlet manifold 175 and medium reactor chamber 162, and medium outlet channels 1105 between medium reactor chamber 162 and medium outlet manifold 180.

In one embodiment, end plate 130 may be solid except for bolt holes 135.

In one embodiment, plates 110, 115, 120, 125, and 130 are bolted together by placing bolts 1110 in bolt holes 135 in the corners of the plates, as shown in FIG. 2. There may additionally be gaskets 1115 between plates 110, 115, 120, 125, and 130 to seal bioreactor 100.

In one embodiment, $H_2$ gas may enter bioreactor 100 through gas inlet 140 in manifold plate 110, and may flow through gas inlet channels 185 in gas delivery plate 115 into gas reactor chamber 160, where the gas is available for use by the biomaterial on membrane 195 in biomaterial reactor chamber 161. The gas flows out through gas outlet channels 190 to gas outlet manifold 170, and exits bioreactor 100 through gas outlet 145 in manifold plate 110.

In one embodiment, medium may enter bioreactor 100 though medium inlet 150 in manifold plate 110. In one embodiment, $O_2$ and $CO_2$ are mixed in the medium. Medium flows through medium inlet manifold 175 in gas delivery plate 115, biomaterial plate 120, and medium delivery plate 125. The medium flows through medium inlet channels 1100 to medium reactor chamber 162 in medium delivery plate 125, where the medium is available for use by the biomaterial in biomaterial reactor chamber 161 of biomaterial plate 120. The medium flows out through medium outlet channels 1105 to medium outlet manifold 180 in medium delivery plate 125, biomaterial plate 120, and gas delivery plate 115. The medium exits bioreactor 100 through medium outlet 155 in manifold plate 110.

Alternatively, $CO_2$ may be supplied with the $H_2$ gas; or $CO_2$ may be supplied with both the $H_2$ gas and the medium. Alternatively, in one embodiment, a different gas may be introduced from each side (such as $H_2/O_2$) of the biomaterial reactor chamber, and the medium may be flowed slowly through the biomaterial reactor chamber to provide mixing within the biomaterial reactor chamber. In such an embodiment, of course, the innermost membranes about the biomaterial may be hydrophobic.

In one embodiment, membrane 195 in biomaterial plate 120 mitigates or governs the concentrations of reactants in the interaction between the $H_2$ gas in gas reactor chamber 160 in gas delivery plate 115 and the $CO_2$ and the $O_2$ in the medium in medium reactor chamber 162 in medium delivery plate 125. In one embodiment, the biomaterial on membrane 195 may consume the $H_2$ from gas reactor chamber 160 in gas delivery plate 115 and the $CO_2$ and $O_2$ in the medium in medium reactor chamber 162 in medium delivery plate 125 and metabolizes them to the bio-based product. In one embodiment, the bio-based product may flow out with the medium and can be separated in a distillation process.

The process is easily scalable by adding plates to the reactor. For example, instead of end plate 130 after medium delivery plate 125, there may be another biomaterial plate 120, and gas delivery plate 115. The addition may be extended to tens or hundreds of plates.

If there is a puncture in membrane 195 and $O_2$ leaks into the $H_2$, there is only a small volume of $H_2$ present in gas reactor chamber 160 in gas delivery plate 115, so any energy discharge if the $O_2$ and $H_2$ ignite would be small. Flame arrestors may also be included to quench any flame front generated to further reduce the danger of explosion. The flame arrestors may be located in one or more of the gas manifolds, the gas reactor chamber, the medium manifolds, or the medium reactor chamber. Suitable flame arrestors include, but are not limited to, wire mesh, or metal, plastic, or ceramic foam materials.

An additional benefit of the use of a rigid open foam material in gas reactor chamber 160 is that the rigid foam will provide structural support to membrane 195. The hydrostatic pressure in medium reactor chamber 162 can be substantial if a large number of biomaterial plates are used and the plates are stacked in the vertical direction. For example, if the assembled bioreactor is 2 m high, medium reactor chamber 162 will see the 2 m head pressure, while gas reactor chamber 160 will see little pressure. At the top of bioreactor 100, neither medium reactor chamber 162 nor gas reactor chamber 160 will see much pressure. Thus, a substantial pressure difference will exist across membrane 195 at the bottom of reactor 100, but not at the top. The bottom of membrane 195 may be subject to substantial stress, which can cause membrane 195 to deform and potentially be damaged. If gas reactor chamber 160 contains a rigid open foam material, gas will flow through the chamber in the same way. The rigid foam will support membrane 195 against the pressure difference between the liquid medium side and the gas side.

If biomaterial is used to generate $H_2$ in situ, a similar plate arrangement may be used with channels to provide the nutrients for the $H_2$-producing biomaterial.

Figure 3:
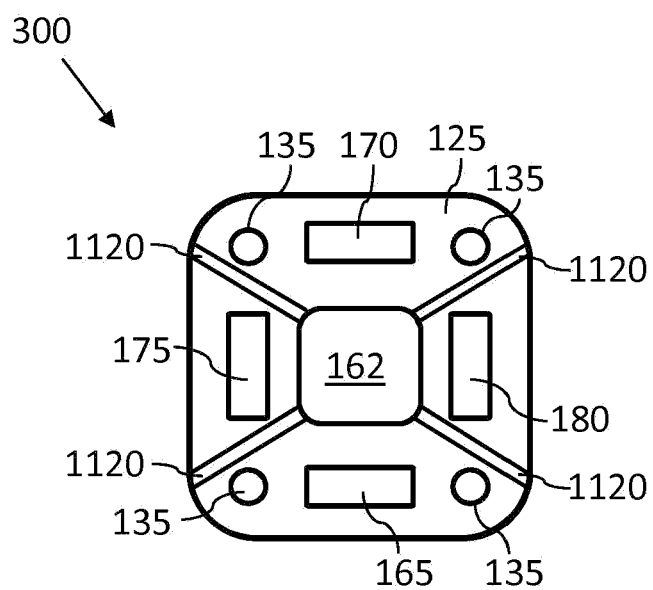
FIG. 3 is an illustration of an alternate embodiment of a medium delivery plate 300.

In bioreactor 100, the rate-limiting step may be oxygen delivery to the biomaterial if the oxygen is dissolved in the medium. In another embodiment, as shown in FIG. 3, there may be one or more ducts 1120 in medium delivery plate 125 from the outside of the reactor into medium reactor chamber 162 to introduce oxygen bubbles into medium reactor chamber 162. Ducts 1120 are positioned to avoid gas and medium manifolds 165, 170, 175, and 180 in medium delivery plate 125. The oxygen bubbles formed are small, e.g., fractions of a millimeter in diameter, and they brush against membrane 195 to provide additional oxygen transfer through membrane 195. Several types of small bubble generation devices, such as porous materials (stones, frits), tees, venturi tubes, and ultrasonic vibrators, can be employed to generate small gas bubbles in the medium.

FIGS. 4A-E and 5 show the design of a membrane assembly 400 for use in biomaterial reactor chamber 161. As shown in FIG. 5, membrane assembly 400 is a stacked composite structure. The end layers 405 are gas- and liquid-permeable layers that provide mechanical support. Suitable gas- and liquid-permeable layers include, but are not limited to, screens made of metal, plastic, ceramic, or composites thereof. The selection will depend on the membrane, medium, and gases used. As shown in FIG. 5, the next layer of membrane assembly 400 is a gas (such as $H_2$) permeable membrane 410. Suitable gas permeable membranes include, but are not limited to, silicone, polyvinylidene difluoride (PVDF), porous polytetrafluoroethylene (PTFE), acrylic copolymer, polycarbonate, polypropylene, and modified nylon.

As shown in FIG. 5, the center layer of membrane assembly 400 is a spacer layer 415 with an inlet tube 420 and an outlet tube 425. In some embodiments, spacer layer 415 is hollow. Inlet tube 420 and outlet tube 425 may be positioned in the corners (or in another convenient location) so that they avoid gas inlet manifold 165, gas outlet manifold 170, medium inlet manifold 175, and medium outlet manifold 180 in bioreactor 100.

As shown in FIG. 5, the next layer of membrane assembly 400 is a liquid permeable membrane 430. Suitable liquid permeable layers include, but are not limited to, woven material, including cloths and meshes, as well as permeable materials such as silicone, PVDF, nitrocellulose, woven material, cloth, mesh, glass fibers, mixed cellulose ester (MCE), polycarbonate, modified polycarbonate, polyethersulfone PES, nylon, ceramic, PTFE, modified PVDF, modified polyacrylonitrile, and modified polypropylene.

Membrane assembly 400 may form a cavity bounded by spacer layer 415 and gas permeable membrane 410 and liquid permeable membrane 430. These membranes can be assembled in the bioreactor 'dry', i.e., without any biomaterial. After the bioreactor is assembled, a biofilm solution loaded with biomaterial can be injected into spacer layer 415 through inlet tube 420 until the cavity fills up completely. The excess biofilm solution can be purged using outlet tube 425. Inlet tube 420 and outlet tube 425 can then be sealed during reactor operation.

Inlet tube 420 and outlet tube 425 can be sealed in any way known to those of skill in the art. Suitable methods include, but are not limited to, valves and rubber septa in the tube or channel that could be punctured with a needle to fill and remove the biomaterial from the cavity.

Once filled, the biofilm solution can be gelled or hardened, if needed, by flowing a solution through the reactor, such as calcium chloride or other divalent cation, which acts to gel the biofilm when it contacts the liquid permeable cloth side. After extended operation, the biofilm can be dissolved by injecting a solution, such as sodium citrate or other suitable de-gelling solution, into the cavity, or by flushing the reactor with the solution. The reactor can be sterilized by injecting a sterilizing solution through inlet tube 420 and removing it through outlet tube 425. The biofilm charge can then be replaced.

Alternatively, there can be a porous material, such as open ceramic foam, in the spacer layer. In this case, the biomaterial could live on the porous material, and a gelled biofilm may not be necessary.

In another embodiment, liquid permeable layer 430 is replaced with a material that has a pore size small enough to retain the biomaterial, but still allow sufficient medium transfer. Suitable materials include, but are not limited to, dialysis tubing, PES, PVDF, nylon mesh, and glass fiber filters. In this configuration, it would not be necessary for the biomaterial to be immobilized in a polysaccharide or similar material. Rather, the biomaterial may be loaded into the cavity at a very high concentration and then flushed from the cavity via the inlet 415 and outlet tubes 420.

Figure 6:
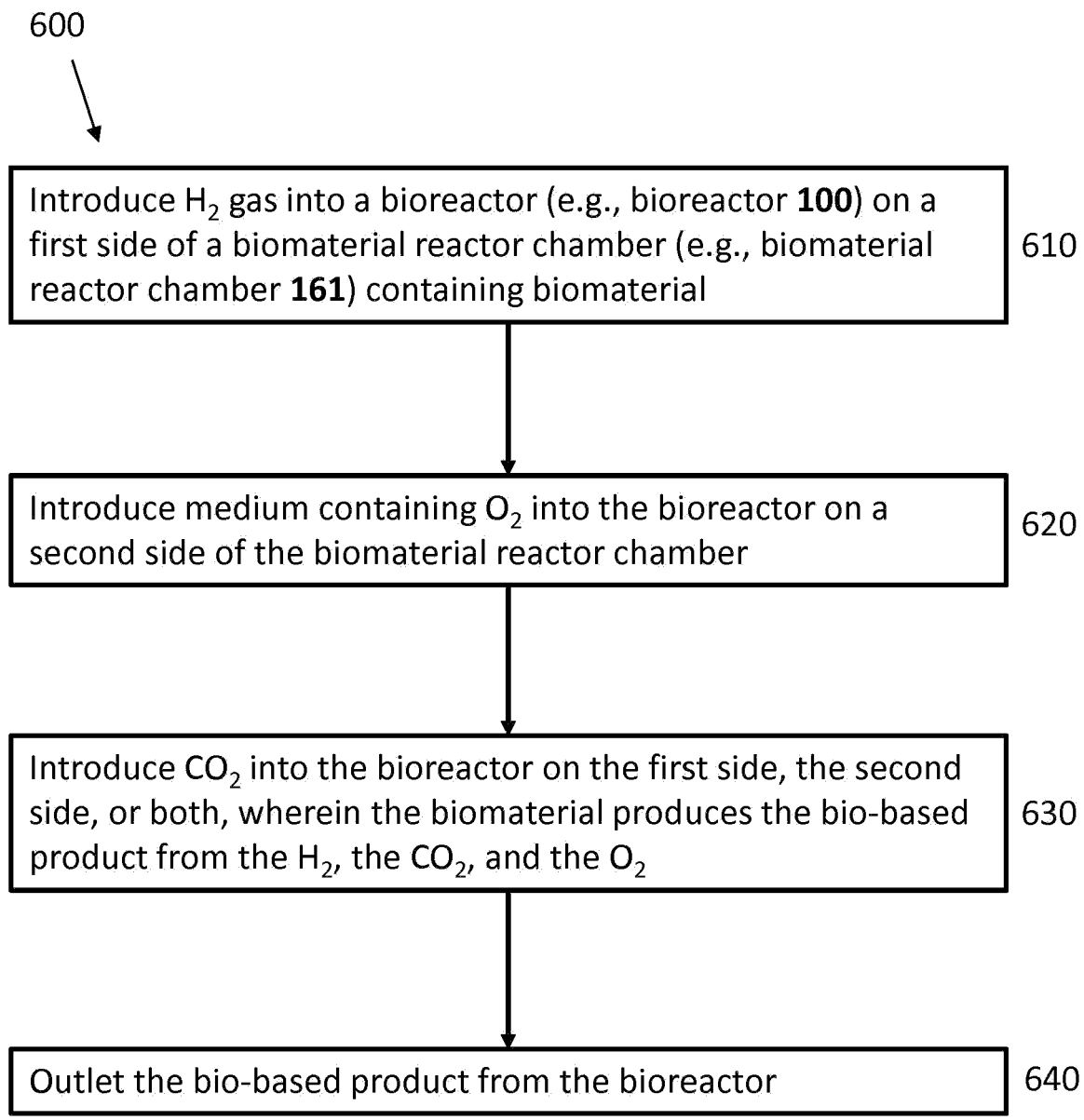
FIG. 6 is a flowchart depicting an example method 600 for making a bio-based product.

FIG. 6 is a flowchart depicting an example method 600 for making a bio-based product. As shown in FIG. 6, the method comprises: introducing $H_2$ gas into a bioreactor (e.g., bioreactor 100) on a first side of a biomaterial reactor chamber (e.g., biomaterial reactor chamber 161) containing biomaterial (step 610); introducing medium containing $O_2$ into the bioreactor on a second side of the biomaterial reactor chamber (step 620); introducing $CO_2$ into the bioreactor on the first side, the second side, or both, wherein the biomaterial produces the bio-based product from the $H_2$, the $CO_2$, and the $O_2$ (step 630); and outletting the bio-based product from the bioreactor (step 640).

In one embodiment, the bio-based product may be outletted from the bioreactor with the medium, with the $H_2$ gas, or with both. Introducing $H_2$ gas into the bioreactor may comprise introducing the $H_2$ gas through a gas inlet to a gas inlet manifold to a gas reactor chamber on the first side of the biomaterial reactor chamber. The $H_2$ gas may be outletted or removed from the gas reactor chamber through a gas outlet manifold and a gas outlet. Alternatively, introducing the medium into the bioreactor may comprise introducing the medium through a medium inlet to a medium inlet manifold to a medium reactor chamber on the second side of the biomaterial reactor chamber. The medium may be outletted or removed from the medium reactor chamber through a medium outlet manifold and a medium outlet. In one embodiment, the bio-based product may be outletted from the bioreactor with the medium and may be separated from the medium by distillation. In another embodiment, the bio-based product may be outletted from the bioreactor with the $H_2$ gas.

In one embodiment, the bioreactor embodying the method comprises: a manifold plate having a gas inlet, a gas outlet, a medium inlet, and a medium outlet; a gas delivery plate having a gas reactor chamber, a gas inlet manifold in fluid communication with the gas reactor chamber, a gas outlet manifold in fluid communication with the gas reactor chamber, a medium inlet manifold in fluid communication with the medium inlet, and a medium outlet manifold in fluid communication with the medium outlet; a biomaterial plate having the biomaterial reactor chamber, a gas inlet manifold in fluid communication with the gas delivery plate gas inlet manifold, a gas outlet manifold in fluid communication with the gas delivery plate gas outlet manifold, a medium inlet manifold in fluid communication with the gas delivery plate medium inlet manifold, and a medium outlet manifold in fluid communication with the gas delivery plate medium outlet manifold; a medium delivery plate having a medium reactor chamber, a gas inlet manifold in fluid communication with the biomaterial plate gas inlet manifold, a gas outlet manifold in fluid communication with the biomaterial plate gas outlet, a medium inlet manifold in fluid communication with the medium reactor chamber and the biomaterial plate medium inlet manifold, and a medium outlet manifold in fluid communication with the medium reactor chamber and the biomaterial plate medium outlet manifold; and an end plate.

Figure 7:
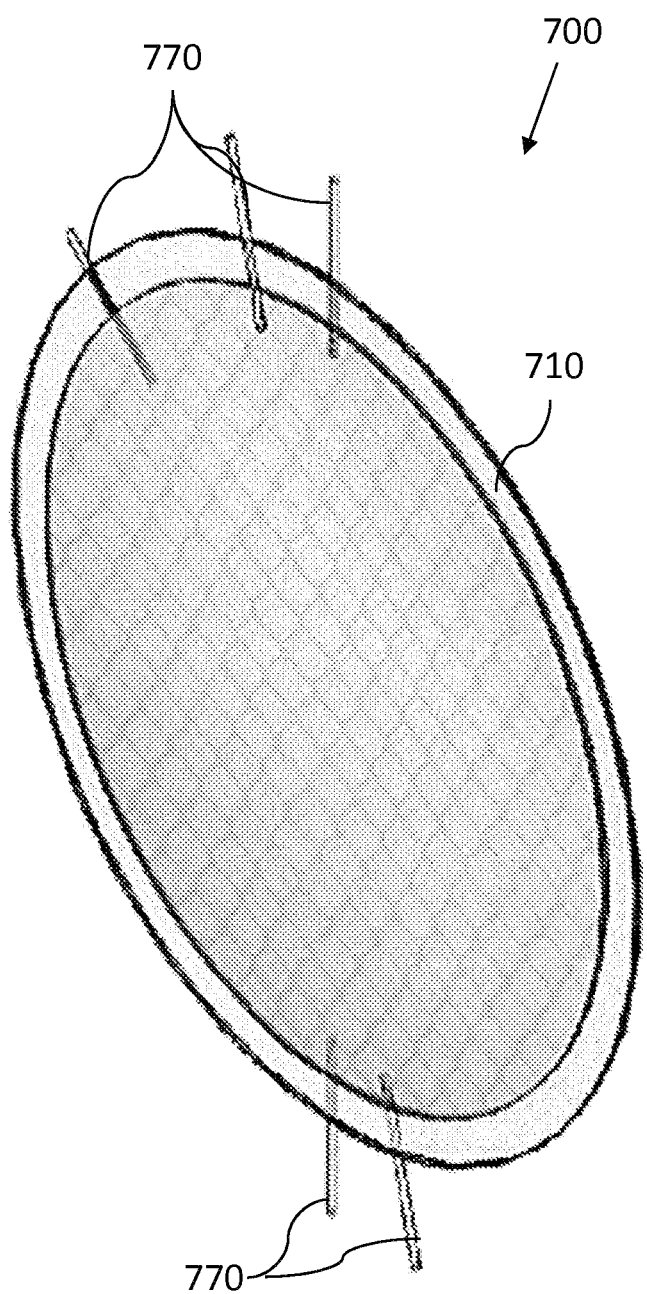
FIG. 7 is an illustration of one embodiment of a membrane assembly 700 for use as a single use gas exchange membrane bioreactor.
Figure 8:
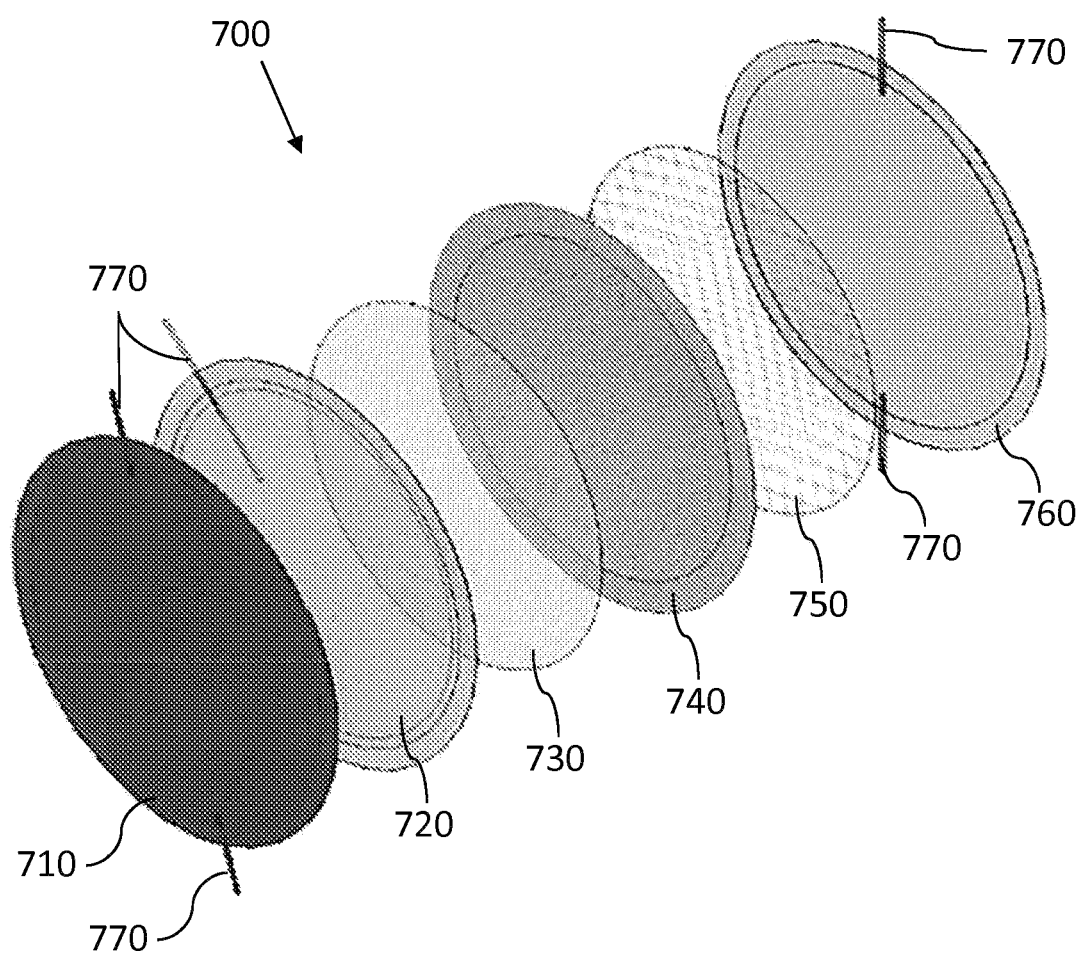
FIG. 8 is an exploded view of one embodiment of membrane assembly 700 for use as a single use gas exchange membrane bioreactor.

FIG. 7 is an illustration of one embodiment of a membrane assembly 700 for use as a single use gas exchange membrane bioreactor. FIG. 8 is an exploded view of one embodiment of membrane assembly 700. As shown in FIG. 8, membrane assembly 700 comprises a first outer shell 710; a hydrophilic membrane 720; a biomaterial 730; a hydrophobic membrane 740; optionally, a flame arrestor 750; and a second outer shell 760.

In one embodiment of the bioreactor of FIG. 8, first outer shell 710 and second outer shell 760 are comprised of the same or a different material comprising at least one of ABS, acrylic, polycarbonate, polyethylene, polypropylene, polyester, and nylon. In one embodiment, hydrophilic membrane 720 may be comprised of a material that is hydrophilic and of a sufficient porosity to retain biomaterial 730 nutrients and medium to pass through it. For example, hydrophilic membrane 720 may be comprised of at least one of modified PVDF, modified polyacrylonitrile, modified polycarbonate, PES, modified polypropylene, PTFE, and nylon. In one embodiment, hydrophilic membrane 720 may be sealed and/or bonded to first outer shell 710 around the outside edges, with inlet and outlet ports 770 to facilitate flow of nutrient-carrying liquid medium. In one embodiment, first outer shell 710 may allow oxygen transfer that dissolves into and saturates the medium to ensure that contained biomaterial 730 is sufficiently supplied with dissolved oxygen. Alternatively, the medium may be internally or externally sparged to ensure sufficient oxygen is available to biomaterial 730.

In one embodiment, biomaterial 730 may be comprised of a living organism capable of using hydrogen gas as a source of energy, including, for example, a bacteria capable of using hydrogen gas as a source of energy. In one embodiment, biomaterial 730 may be comprised of *Ralstonia eutropha*.

In one embodiment, hydrophobic membrane 740 may be comprised of a material that is hydrophobic and of sufficient porosity to retain biomaterial 730 and to allow contact between biomaterial 730 and a gas introduced to feed the system. For example, hydrophobic membrane 740 may be comprised of at least one of silicone, polyvinylidene difluoride (PVDF), porous polytetrafluoroethylene (PTFE), acrylic copolymer, polycarbonate, polypropylene, and modified nylon. In one embodiment, hydrophobic membrane 740 may be sealed and/or bonded to second outer shell 760 around the outside edges, with inlet and outlet ports 770 to facilitate flow of nutrient-carrying liquid medium.

In one embodiment, the interstitial gas delivery space may be filled with flame arrestor 750, which may be comprised of, for example, porous open-cell foam or mesh, to suppress the ignition and/or propagation of a flam if there is a mix of gases.

In one embodiment, hydrophilic membrane 720 and hydrophobic membrane 740 may be heat sealed or welded to each other with an access port to facilitate loading, sampling, or harvesting of biomaterial 730.

EXAMPLES

Example 1

Four stacked membrane reactors were set up with *R. eutropha* H16 embedded in alginate film. 0.002 inch silicone membranes were used between the gas phase and the alginate containing the bacteria, and 0.2 micron filters made from mixed cellulose ester or polycarbonate were used between the medium and the alginate biofilm. The filters were used to prevent bacteria from entering the medium stream while still allowing the medium and oxygen to reach the biofilm. The reactors were successfully operated for two weeks using a complex gas mix (66% $CO_2$, 30% $H_2$, 3% $CH_4$, and 1% CO). Air was sparged into the medium tank to saturate the media with oxygen. After continuous operation for two weeks, the reactors were disassembled for bacteria enumeration and hydrogenase analysis. The alginate had mostly dissolved; however, the bacteria were still contained between the silicone and 0.2 micron membranes. All four reactors had measureable hydrogenase activity, indicating that the bacteria were still viable. The concentration of *R. eutropha* H16 increased by about 50% in the reactors compared to a t=0 extracted sample.

Example 2

Two stacked membrane reactors were set up to compare hydrogen permeability through membrane material between the gas and the bacteria. In the first reactor, a 3 mil silicone membrane was used on the gas side. In the second, the silicone was replaced by a porous, hydrophobic material. Results of this study indicated that the *R. eutropha* H16 within the reactor cavity had grown by day 8, with the hydrophobic membrane increasing cell density by four times and the silicone membrane by 23 times. At day 8, the silicone membrane sample had measureable hydrogenase activity. The hydrophobic membrane sample raw data did indicate that there was some slight hydrogenase activity, but it was not quantifiable, most likely due to the low number of cells in the sample. At 14 days, the bacteria concentration in both reactors had increased to similar levels and had measurable hydrogenase activity.

Example 3

*Acidithiobacillus thiooxidans* is an acidophilic obligate autotroph able to use reduced sulfur compounds as an energy source resulting in the production of sulfuric acid. *A. thiooxidans* requires carbon dioxide as a carbon source and molecular oxygen as an electron acceptor for the generation of energy through the reduction of sulfur. Oxygen consumption can be measured through sulfate production. Carbon dioxide consumption can be measured by enumeration of viable free cells produced that are not bound to the sulfur. Because two gases are required for energy production and growth, this testing demonstrates the unique gas transfer system of the disk stack reactor. The reactor was loaded using the silicone and hydrophilic membranes, with the organism contained between them. Carbon dioxide gas was delivered via the silicone side membrane. Oxygen was delivered dissolved in the growth medium through the hydrophilic membrane, as it was for *R. eutropha* H16. Adequate delivery of oxygen will allow for acid production, while carbon dioxide delivery will allow for assimilation and growth. The results show increased sulfate concentration and a release of free viable cells indicating cell growth. This example shows the versatility of the design by using another organism that requires liquid media feed through a hydrophilic membrane and gas feed through the silicone membrane. The example further shows that the reactor can support growth as well as sulfate production.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It is understood that various changes may be made in the function and arrangement of elements described in an exemplary embodiment without departing from the scope of the invention as set forth in the appended claims.

The invention claimed is:

1. A bioreactor, comprising:
 a biomaterial reactor chamber comprising a membrane assembly, the membrane assembly configured for use as a gas exchange membrane bioreactor, the membrane assembly comprising:
 a first outer shell;
 a hydrophilic membrane with pore size about 0.2 μm or less;
 a biomaterial comprising a bacteria capable of using hydrogen gas as a source of energy;
 a hydrophobic membrane; and
 a second outer shell,
 wherein the hydrophobic membrane and the hydrophobic membrane are heat sealed or welded to each other with at least one access port configured effective to facilitate loading, sampling, or harvesting of the biomaterial.

2. The bioreactor of claim 1, the membrane assembly being configured as a single-use gas exchange membrane bioreactor.

3. The bioreactor of claim 1, the first outer shell and the second outer shell of the membrane assembly comprising the same or different material comprising at least one of: ABS, acrylic, polycarbonate, polyethylene, polypropylene, polyester, and nylon.

4. The bioreactor of claim 1, comprising one or more of:
 the hydrophilic membrane of the membrane assembly comprising at least one of: modified PVDF, modified polyacrylonitrile, modified polycarbonate, PES, modified polypropylene, PTFE, and nylon; and
 the hydrophobic membrane of the membrane assembly comprising at least one of: silicone, pollyvinylidene difluoride (PVDF), porous polytetrafluoroethylene (PTFE), acrylic copolymer, polycarbonate, polypropylene, and modified nylon.

5. The bioreactor of claim 1, comprising one or more of:
 the hydrophilic membrane of the membrane assembly being characterized by a liquid permeability effective to retain the biomaterial and to pass nutrients and liquid medium;
 the hydrophobic membrane of the membrane assembly being characterized by a gas permeability effective to retain the biomaterial and to pass a gas through the hydrophobic membrane to contact the biomaterial; and
 the first outer shell of the membrane assembly being characterized by an oxygen permeability effective to allow oxygen to contact the biomaterial.

6. The bioreactor of claim 1, the membrane assembly comprising a spacer layer.

7. The bioreactor of claim 6, the membrane assembly comprising a cavity formed by the spacer layer, the hydrophobic membrane, and the hydrophilic membrane.

8. The bioreactor of claim 1, comprising one or more of:
 the hydrophilic membrane and the first outer shell of the membrane assembly comprising corresponding outside edges, the hydrophilic membrane being sealed and/or bonded to the first outer shell around the outside edges; and
 the hydrophobic membrane and second first outer shell of the membrane assembly comprising corresponding outside edges, the hydrophobic membrane being sealed and/or bonded to the second outer shell around the outside edges.

9. The bioreactor of claim 1, the membrane assembly further comprising one or more of each of an inlet port and an outlet port, the inlet and outlet ports being configured effective to one or more of: direct a liquid in and out of the membrane assembly; and direct oxygen to sparge a liquid in the membrane assembly.

10. The bioreactor of claim 1, the biomaterial comprising *Ralstonia eutropha*.

11. The bioreactor of claim 1, the membrane assembly further comprising a flame arrestor.

12. The bioreactor of claim 1, the membrane assembly comprising at least one of an artificial biofilm and a natural biofilm configure effective to immobilize the biomaterial.

13. A bioreactor, comprising:
 a biomaterial reactor chamber comprising a membrane assembly, the membrane assembly configured for use as a gas exchange membrane bioreactor, the membrane assembly comprising:
 a first outer shell;
 a hydrophilic membrane;
 a biomaterial;

a hydrophobic membrane;

a flame arrestor; and a second outer shell, wherein the hydrophilic membrane and the hydrophobic membrane are heat sealed or welded to each other with at least one access port configured effective to facilitate loading, sampling, or harvesting of the biomaterial.

14. The bioreactor of claim 13, further comprising:

a gas reactor chamber in fluid communication with a first side of the biomaterial reactor chamber;

a medium reactor chamber in fluid communication with a second side of the biomaterial reactor chamber;

a gas inlet and a gas outlet in fluid communication with the gas reactor chamber;

and a medium inlet and a medium outlet in fluid communication with the medium reactor chamber.

15. The bioreactor of claim 13, wherein the flame arrestor comprises at least one of: a porous open-cell foam and a mesh.

16. The bioreactor of claim 14, further comprising a flame arrestor in one or more of the gas reactor chamber, the gas inlet, the gas outlet, the medium reactor chamber, the medium inlet, and the medium outlet.

* * * * *